US010561424B2

(12) United States Patent
Penna et al.

(10) Patent No.: US 10,561,424 B2
(45) Date of Patent: Feb. 18, 2020

(54) METHODS OF INSERTING A CIRCULAR STAPLING APPARATUS INTO A BODY LUMEN

(71) Applicant: Covidien LP, Mansfield, MA (US)

(72) Inventors: Christopher Penna, Guilford, CT (US); Boris Vestweber, Pembroke (BM)

(73) Assignee: Covidien LP, Mansfield, MA (US)

( * ) Notice: Subject to any disclaimer, the term of this patent is extended or adjusted under 35 U.S.C. 154(b) by 308 days.

(21) Appl. No.: 15/607,986

(22) Filed: May 30, 2017

(65) Prior Publication Data
US 2017/0325815 A1 Nov. 16, 2017

Related U.S. Application Data

(63) Continuation-in-part of application No. 14/996,467, filed on Jan. 15, 2016, now Pat. No. 10,076,332, and
(Continued)

(30) Foreign Application Priority Data

May 20, 2011 (DE) .................. 10 2011 102 686

(51) Int. Cl.
*A61B 17/115* (2006.01)
*A61B 17/11* (2006.01)
(Continued)

(52) U.S. Cl.
CPC ........ *A61B 17/1152* (2013.01); *A61B 17/068* (2013.01); *A61B 17/105* (2013.01);
(Continued)

(58) Field of Classification Search
CPC ............... A61B 17/105; A61B 17/064; A61B 2017/07271; A61B 2017/2927;
(Continued)

(56) References Cited

U.S. PATENT DOCUMENTS

| 4,473,077 A | 9/1984 | Noiles et al. |
| 4,576,167 A | 3/1986 | Noiles |

(Continued)

FOREIGN PATENT DOCUMENTS

| DE | 102007057207 A1 | 5/2009 |
| DE | 202011101205 U1 | 8/2012 |

(Continued)

OTHER PUBLICATIONS

European Search Report dated Dec. 11, 2013 from counterpart EP Application No. EP13183338.6 (8 pgs).
(Continued)

*Primary Examiner* — Katherine M Shi

(57) ABSTRACT

A method of inserting a circular stapling apparatus into a body lumen includes inserting a distal portion of a shell assembly of the circular stapling apparatus in an entrance to a body lumen, introducing an insufflation fluid through an aperture defined in an outer surface of the shell assembly, and inserting a remainder of the shell assembly and a portion of an elongated member into the body lumen. Introducing the insufflation fluid through the aperture flows insufflation fluid into the body lumen.

16 Claims, 14 Drawing Sheets

Related U.S. Application Data a continuation-in-part of application No. 14/117,206, filed on Nov. 7, 2014, which is a continuation of application No. 14/011,103, filed as application No. PCT/EP2011/003609 on Jul. 19, 2011, now Pat. No. 9,265,503.

(60) Provisional application No. 61/698,148, filed on Sep. 7, 2012.

(51) Int. Cl.
*A61B 17/10* (2006.01)
*A61B 17/068* (2006.01)
*A61B 17/32* (2006.01)

(52) U.S. Cl.
CPC ............ *A61B 17/11* (2013.01); *A61B 17/115* (2013.01); *A61B 17/1155* (2013.01); *A61B 17/32* (2013.01); *A61B 2217/007* (2013.01)

(58) Field of Classification Search
CPC .............................................................................
A61B 2017/07214; A61B 2017/07221; A61B 17/07207; A61B 17/115; A61B 17/072; A61B 17/1155; A61B 17/1114; A61B 17/068
USPC .............................. 606/153; 227/175.1–182.1
See application file for complete search history.

(56) References Cited

U.S. PATENT DOCUMENTS

| | | | |
|---|---|---|---|
| 4,646,745 A | 3/1987 | Noiles | |
| 5,005,749 A | 4/1991 | Aranyi | |
| 5,119,983 A | 6/1992 | Green et al. | |
| 5,395,030 A | 3/1995 | Kuramoto et al. | |
| 5,403,326 A | 4/1995 | Harrison et al. | |
| 5,483,951 A | 1/1996 | Frassica et al. | |
| 5,588,579 A | 12/1996 | Schnut et al. | |
| 5,868,760 A | 2/1999 | McGuckin, Jr. | |
| 6,053,390 A | 4/2000 | Green et al. | |
| 6,083,241 A | 7/2000 | Longo et al. | |
| 6,102,271 A | 8/2000 | Longo et al. | |
| 6,119,913 A | 9/2000 | Adams et al. | |
| 6,126,058 A | 10/2000 | Adams et al. | |
| 6,142,933 A | 11/2000 | Longo et al. | |
| 6,179,195 B1 | 1/2001 | Adams et al. | |
| 6,241,140 B1 | 6/2001 | Adams et al. | |
| 6,264,086 B1 | 7/2001 | McGuckin, Jr. | |
| 6,302,311 B1 | 10/2001 | Adams et al. | |
| 6,343,731 B1 | 2/2002 | Adams et al. | |
| 6,451,029 B1 | 9/2002 | Yeatman | |
| 6,478,210 B2 | 11/2002 | Adams et al. | |
| 6,585,144 B2 | 7/2003 | Adams et al. | |
| 6,601,749 B2 | 8/2003 | Sullivan et al. | |
| 6,605,078 B2 * | 8/2003 | Adams | A61B 1/00087 600/104 |
| 6,629,630 B2 | 10/2003 | Adams | |
| 6,632,227 B2 | 10/2003 | Adams | |
| 6,695,198 B2 | 2/2004 | Adams et al. | |
| 6,820,791 B2 | 11/2004 | Adams | |
| 6,827,246 B2 | 12/2004 | Sullivan et al. | |
| 6,840,423 B2 | 1/2005 | Adams et al. | |
| 6,866,178 B2 | 3/2005 | Adams et al. | |
| 6,874,669 B2 | 4/2005 | Adams et al. | |
| 6,959,851 B2 | 11/2005 | Heinrich | |
| 7,083,630 B2 | 8/2006 | DeVries et al. | |
| 7,090,684 B2 | 8/2006 | McGuckin, Jr. et al. | |
| 7,810,690 B2 | 10/2010 | Bilotti et al. | |
| 8,181,840 B2 | 5/2012 | Milliman | |
| 9,265,503 B2 | 2/2016 | Vestweber | |
| 2002/0020732 A1 | 2/2002 | Adams et al. | |
| 2002/0047036 A1 | 4/2002 | Sullivan et al. | |
| 2002/0063143 A1 | 5/2002 | Adams et al. | |
| 2003/0019905 A1 | 1/2003 | Adams et al. | |
| 2003/0127491 A1 | 7/2003 | Adams et al. | |
| 2003/0132267 A1 | 7/2003 | Adams et al. | |
| 2003/0144675 A1 | 7/2003 | Nicolo | |
| 2003/0192937 A1 | 10/2003 | Sullivan et al. | |
| 2004/0134964 A1 | 7/2004 | Adams et al. | |
| 2004/0193184 A1 | 9/2004 | Laufer et al. | |
| 2004/0217146 A1 | 11/2004 | Beck | |
| 2004/0232198 A1 | 11/2004 | Adams et al. | |
| 2005/0145675 A1 | 7/2005 | Hartwick et al. | |
| 2005/0205640 A1 | 9/2005 | Milliman | |
| 2006/0108393 A1 | 5/2006 | Heinrich et al. | |
| 2006/0151568 A1 | 7/2006 | Weller et al. | |
| 2006/0155308 A1 | 7/2006 | Griego | |
| 2006/0191975 A1 | 8/2006 | Adams et al. | |
| 2006/0241692 A1 | 10/2006 | McGuckin et al. | |
| 2007/0023475 A1 | 2/2007 | Csiky | |
| 2007/0032797 A1 * | 2/2007 | Ortiz | A61B 17/064 606/142 |
| 2007/0233161 A1 | 10/2007 | Weller et al. | |
| 2008/0004566 A1 | 1/2008 | Sloan | |
| 2010/0001037 A1 | 1/2010 | Racenet et al. | |
| 2010/0163598 A1 | 7/2010 | Belzer | |
| 2015/0060525 A1 * | 3/2015 | Vestweber | A61B 17/1114 227/180.1 |
| 2017/0325817 A1 * | 11/2017 | Racenet | A61B 17/1155 |

FOREIGN PATENT DOCUMENTS

| | | |
|---|---|---|
| EP | 1652481 A2 | 5/2006 |
| EP | 2353520 A2 | 8/2011 |
| EP | 3243449 A2 | 11/2017 |

OTHER PUBLICATIONS

European Search Report dated Oct. 31, 2018 issued in EP 18174874.

* cited by examiner

METHODS OF INSERTING A CIRCULAR STAPLING APPARATUS INTO A BODY LUMEN

CROSS-REFERENCE TO RELATED APPLICATIONS

This application is a continuation-in-part of U.S. patent application Ser. No. 14/996,467, filed Jan. 15, 2016, which is a continuation of U.S. patent application Ser. No. 14/011,103, filed Aug. 27, 2013, now U.S. Pat. No. 9,265,503, which claims the benefit of, and priority to, U.S. Provisional Patent Application Ser. No. 61/698,148, filed Sep. 7, 2012.

In addition, this application is a continuation-in-part of U.S. patent application Ser. No. 14/117,206, filed Nov. 7, 2014, which is a national stage of PCT/EP11/03609, filed Jul. 19, 2011, which claims the benefit of, and priority to, German Patent Application No. 10 2011 102 686.3, filed May 20, 2011.

The entire contents of each of the above applications are hereby incorporated by reference.

BACKGROUND

Technical Field

The present disclosure relates to circular surgical staplers and channel guides for use therewith. More particularly, the present disclosure relates to circular surgical staplers and their methods of use including a shell assembly having a port in communication with a body lumen.

Description of Related Art

Circular stapling apparatuses may be used in endoscopic procedures, laparoscopic procedures, or through natural body orifices, for fastening tissue. The circular stapling apparatuses may be powered or manually-operated and may include a tool assembly that is configured to operably couple to a distal end of an elongated member that extends from a handle assembly. The handle assembly may be reusable and the tool assembly may be disposable. The tool assembly may include an anvil assembly and a cartridge assembly that houses one or more fasteners therein.

In use, a circular stapling apparatus (or circular surgical staplers) may be used to reattach rectum portions that were previously transected. In this instance, a physician may insert a distal end (including an anvil assembly) of the circular stapling apparatus into a rectum of a patient and maneuver the distal end up the colonic tract of the patient toward the transected rectum portions. The physician may also insert the remainder of the circular stapling apparatus (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis.

After the end-to-end anastomosis has been effected, the circular stapling apparatus is removed from the surgical site. The physician may use a sigmoidoscope or other suitable device to inspect the anastomosis for bleeding, patency, and/or blood perfusion. In certain instances, the physician uses the sigmoidoscope to introduce $CO_2$ into the colonic tract to check for leaks adjacent the anastomosis.

While the aforementioned circular stapling apparatuses are suitable for their intended purposes, it may be beneficial to provide a circular stapling apparatus including a port to provide a passageway to the surgical site, as doing so may reduce the amount of instruments and/or incisions necessary to perform the surgical procedure. Additionally, it may be beneficial to provide a channel guide for use with a circular stapling apparatus, as doing so may reduce the amount of instruments and/or incisions necessary to perform the surgical procedure.

SUMMARY

The present disclosure relates to an end effector for use with a circular stapling apparatus. The end effector includes a shell assembly, a port and a stepped lumen. The shell assembly is configured to support a cartridge assembly thereon. The shell assembly includes an outer wall. The port is disposed on the outer wall of the shell assembly. The stepped lumen is disposed in fluid communication with the port, and extends through the outer wall of the shell assembly.

In disclosed embodiments, the stepped lumen includes a first portion disposed in fluid communication with the port, and a second portion disposed in fluid communication with the first portion. The first portion is disposed at a first angle with respect to the second portion. It is disclosed that the first angle may be between about 120° and about 150°, or equal to about 135°.

It is further disclosed that the stepped lumen includes a third portion disposed in fluid communication with the second portion. The second portion is disposed at a second angle with respect to the third portion. It is disclosed that the second angle may be between about 120° and about 150°, or equal to about 135°. In disclosed embodiments, the first angle is equal to the second angle.

The present disclosure also relates to a method of performing a surgical procedure. The method comprises positioning a channel guide in engagement with a circular stapling apparatus such that an elongate passageway of the channel guide is disposed externally to and adjacent an elongated member of the circular stapling apparatus, aligning an aperture of a mounting portion of the channel guide with an opening of a shell assembly of the circular stapling apparatus, performing a surgical procedure with the circular stapling apparatus, and introducing at least one of a fluid or a device through the elongate passageway of the channel guide and through the aperture of the mounting portion of the channel guide.

In disclosed embodiments, positioning the channel guide in engagement with the circular stapling apparatus includes moving the mounting portion of the channel guide in a distal-to-proximal direction to mechanically engage the shell assembly of the circular stapling apparatus.

It is further disclosed that the method includes rotating a mounting portion of the channel guide with respect to the shell assembly while the channel guide is engaged with the circular stapling apparatus.

Additionally, it is disclosed that introducing at least one of a fluid or a device through the aperture of the mounting portion includes delivering fluid distally through the elongate passageway of the channel guide, through the aperture, and to a surgical site.

In disclosed embodiments, introducing at least one of a fluid or a device through the aperture of the mounting portion includes removing fluid from a surgical site through the aperture of the channel guide and proximally through the elongate passageway of the channel guide.

It is further disclosed that introducing at least one of a fluid or a device through the aperture of the mounting portion includes advancing a camera distally through the elongate passageway of the channel guide, through the aperture, and to a surgical site.

Additionally, it is disclosed that introducing at least one of a fluid or a device includes introducing at least one of a guide wire or an endoscopic camera through the elongate passageway of the channel guide, through the aperture, and to a surgical site.

In aspects of the present disclosure, a method of inserting a circular stapling apparatus into a body lumen includes inserting a distal portion of a shell assembly of the circular stapling apparatus in an entrance to a body lumen, introducing an insufflation fluid through an aperture defined in an outer surface of the shell assembly, and inserting a remainder of the shell assembly and a portion of an elongated member of the circular stapling apparatus into the body lumen. Introducing the insufflation fluid through the aperture flows insufflation fluid into the body lumen.

In aspects, introducing the insufflation fluid through the aperture includes inserting a hose through the port such that the hose extends from within the shell assembly and into the body lumen. Introducing the insufflation fluid through the aperture may include the insufflation fluid being a liquid that lubricates the body lumen. Additionally or alternatively, introducing the insufflation fluid through the aperture may include increasing a volume of the body lumen.

In some aspects, the method includes engaging a channel guide with the aperture of the shell assembly. Engaging the channel guide with the aperture of the shell assembly may include positioning a mounting portion of the channel guide about the shell assembly. Introducing the insufflation fluid through the aperture includes introducing the insufflation fluid through a passageway that is defined by the channel guide. The passageway may be in fluid communication with the aperture.

In certain aspects, engaging the engaging the channel guide with the aperture of the shell assembly includes inserting a nipple of the channel guide into the aperture of the shell assembly. Inserting the nipple of the channel guide into the aperture may include securing the nipple to the shell assembly with tabs that extend from the nipple. Engaging the channel guide with the aperture of the shell assembly may occur after inserting the distal portion of the shell assembly of the circular stapling apparatus into a body lumen.

In particular aspects, engaging the channel guide with the aperture of the shell assembly includes moving the mounting portion of the channel guide in a distal-to proximal direction to mechanically engage the shell assembly. The method may include rotating the mounting portion of the channel guide with respect to the shell assembly while the channel guide is engaged with the circular stapling apparatus. The method may include advancing a camera distally through the channel guide, through the aperture, and to a surgical site. Additionally or alternatively, the method may include advancing a guide wire through the channel guide, through the aperture, and to a surgical site.

In another aspect of the present disclosure, a method of removing a circular stapling apparatus from a body lumen includes withdrawing a distal portion of a shell assembly of a circular stapling apparatus from a body lumen and introducing an insufflation fluid through an aperture defined in an outer surface of the shell assembly such that the insufflation fluid flows into the body lumen while withdrawing the distal portion.

In aspects, introducing the insufflation fluid through the aperture includes supplying the insufflation fluid through a hose in communication with the port such that the hose extends from within the shell assembly into the body lumen. Introducing the insufflation fluid through the aperture may include the insufflation fluid being a liquid which lubricates the body lumen. Introducing the insufflation fluid through the aperture may include increasing a volume of the body lumen.

Further, to the extent consistent, any of the aspects and/or embodiments described herein may be used in conjunction with any or all of the other aspects described herein.

BRIEF DESCRIPTION OF THE DRAWING

Various embodiments of the present disclosure are described hereinbelow with references to the drawings, wherein.

DETAILED DESCRIPTION

Particular embodiments of the present circular surgical staplers will be described herein with reference to the accompanying figures. As shown in the figures and as described throughout the following description, and as is traditional when referring to relative positioning on an object, the term "proximal" refers to the portion of the device that is closer to the user and the term "distal" refers to the portion of the device that is farther from the user. In the following description, well-known functions or constructions are not described in detail to avoid obscuring the present disclosure in unnecessary detail.

Figure 1:
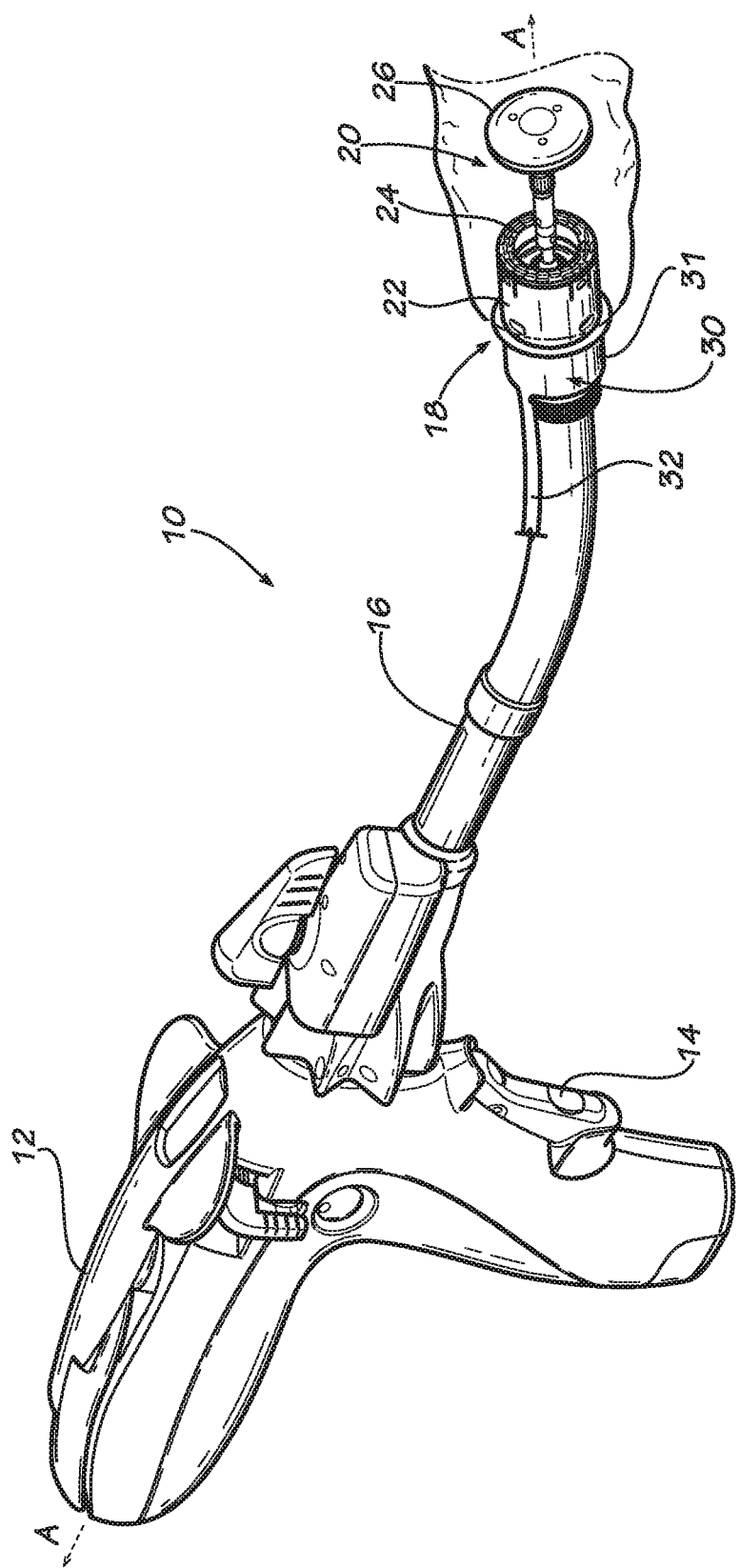
FIG. 1 is a perspective view of a powered circular stapling apparatus including a channel guide engaged therewith, and with a distal end of the circular stapling apparatus disposed within tissue, in accordance with embodiments of the present disclosure.

FIG. 1 illustrates a powered circular stapling apparatus 10 in accordance with embodiments of the present disclosure. Generally, circular stapling apparatus 10 includes a housing or handle assembly 12 having an actuator 14, and an elongated member 16 extending distally from handle assembly 12. In the illustrated embodiment, elongated member 16 is curved. However, it is envisioned that the elongated member 16 may be linear to suit a particular surgical procedure, e.g., mucosectomy, hemorrhoidectomy, etc. A tool assembly 18 (e.g., a multi-use loading unit, or a single-use loading unit) is coupled to or is configured to operably couple to a distal end of elongated member 16 and includes an end effector 20. In disclosed embodiments, a proximal portion of the tool assembly 18 is formed as a single component with the elongated member 16.

Figure 8:
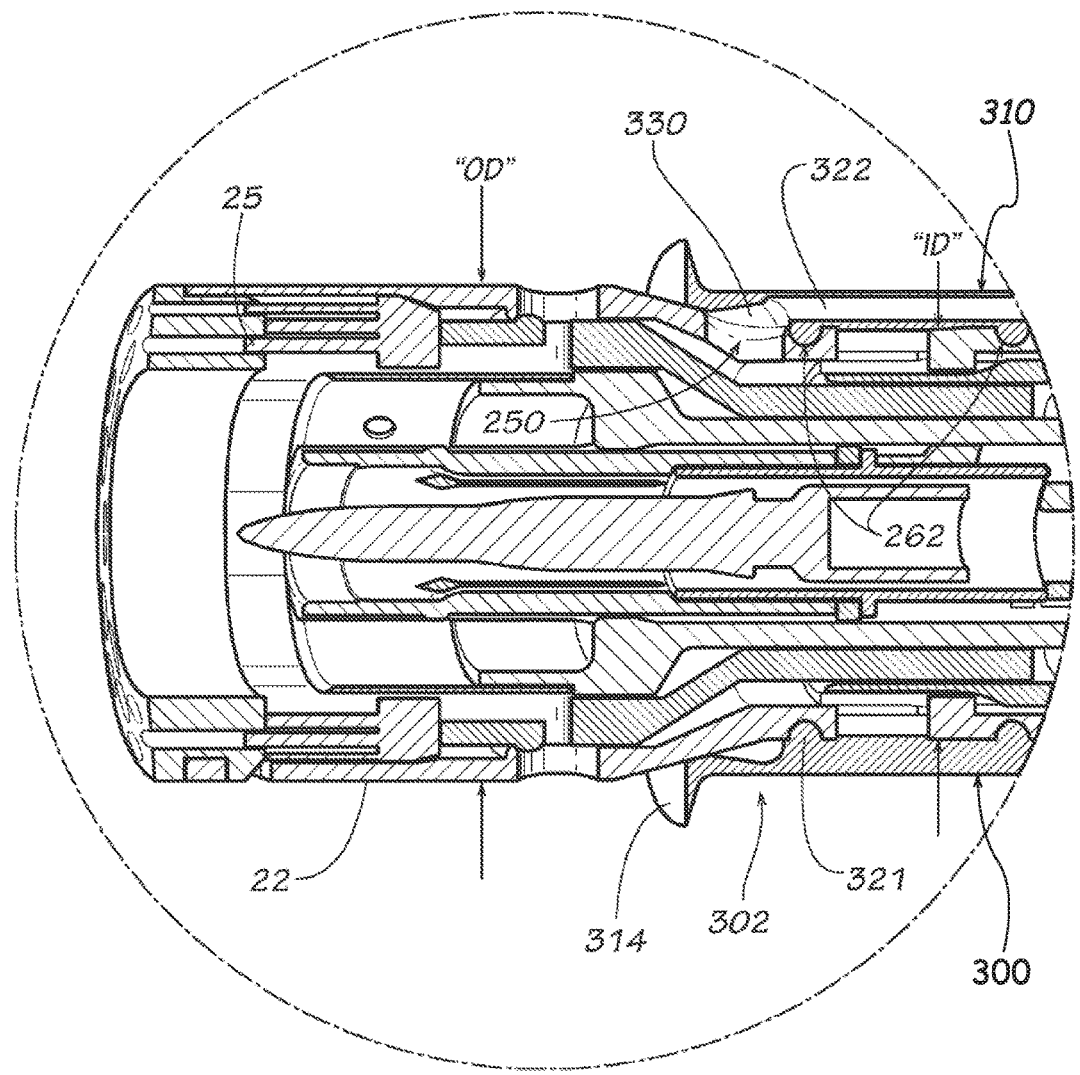
FIG. 8 is the indicated area of detail shown in FIG. 7.
Figure 9:
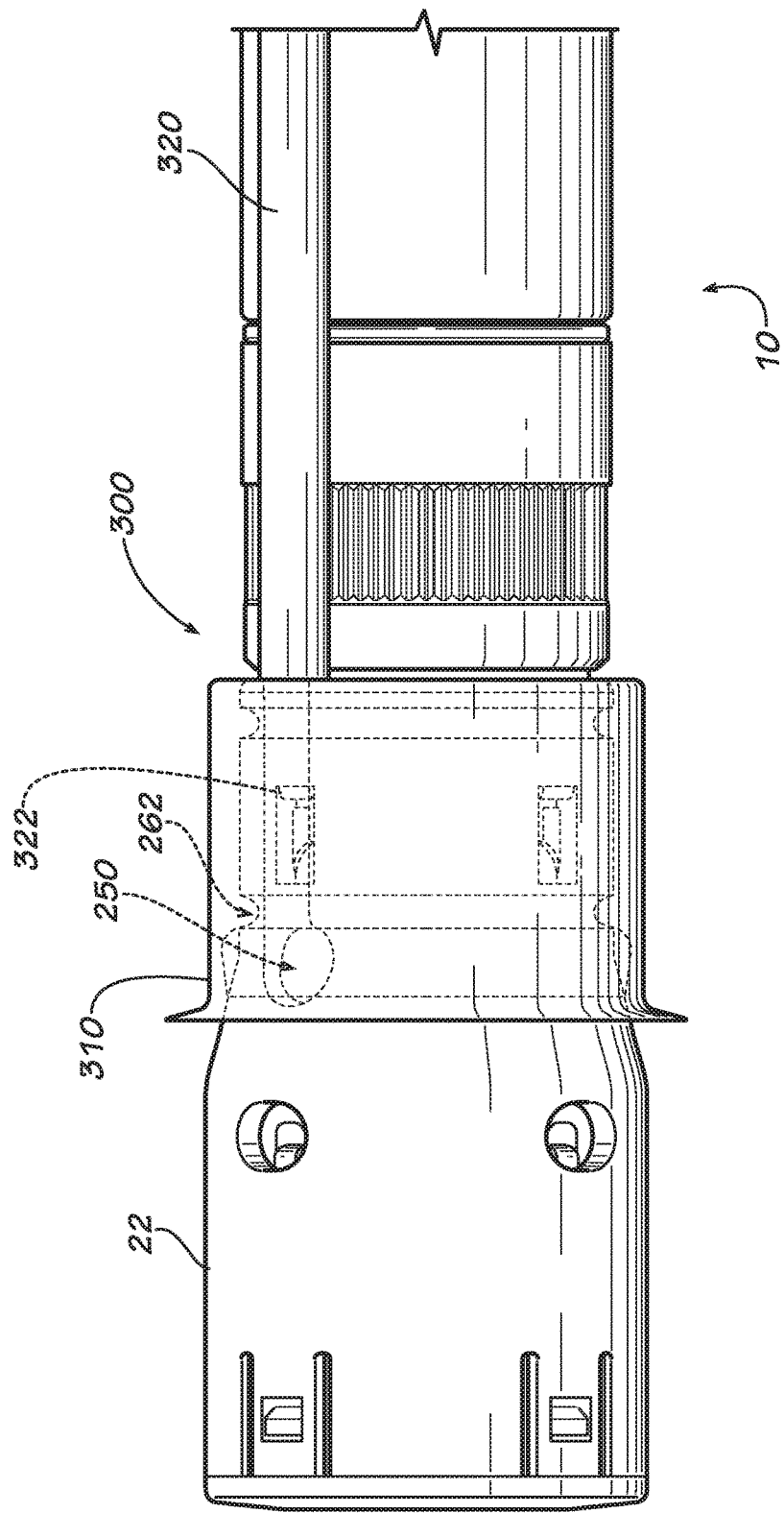
FIG. 9 is a side view of a distal portion of the circular stapling apparatus shown in FIG. 6 engaged with a portion of the channel guide

End effector 20 includes a shell assembly 22 that is configured to support a cartridge assembly 24 thereon. Cartridge assembly 24 is configured to house a plurality of fasteners (not shown) and includes a corresponding plurality of pusher members 25 (FIG. 8) that are operatively engagable with the fasteners to eject the fasteners from the cartridge assembly 24. While fasteners are not shown in the accompanying figures, it is known in the art to include fasteners within a cartridge assembly. As such, the present disclosure includes a cartridge assembly 24 with a plurality of fasteners housed therein.

End effector 20 also includes an anvil assembly 26 that is supported to move in relation to the cartridge assembly 24 between spaced and approximated positions. Anvil assembly 26 includes a plurality of pockets or depressions (not explicitly shown) that are each configured to receive and deform a fastener when the fasteners are deployed from cartridge assembly 24. Additionally, a channel guide 30 including a mounting portion 31 and an elongate passageway 32 is coupled to the shell assembly 22 as described in further detail below.

Figure 2:
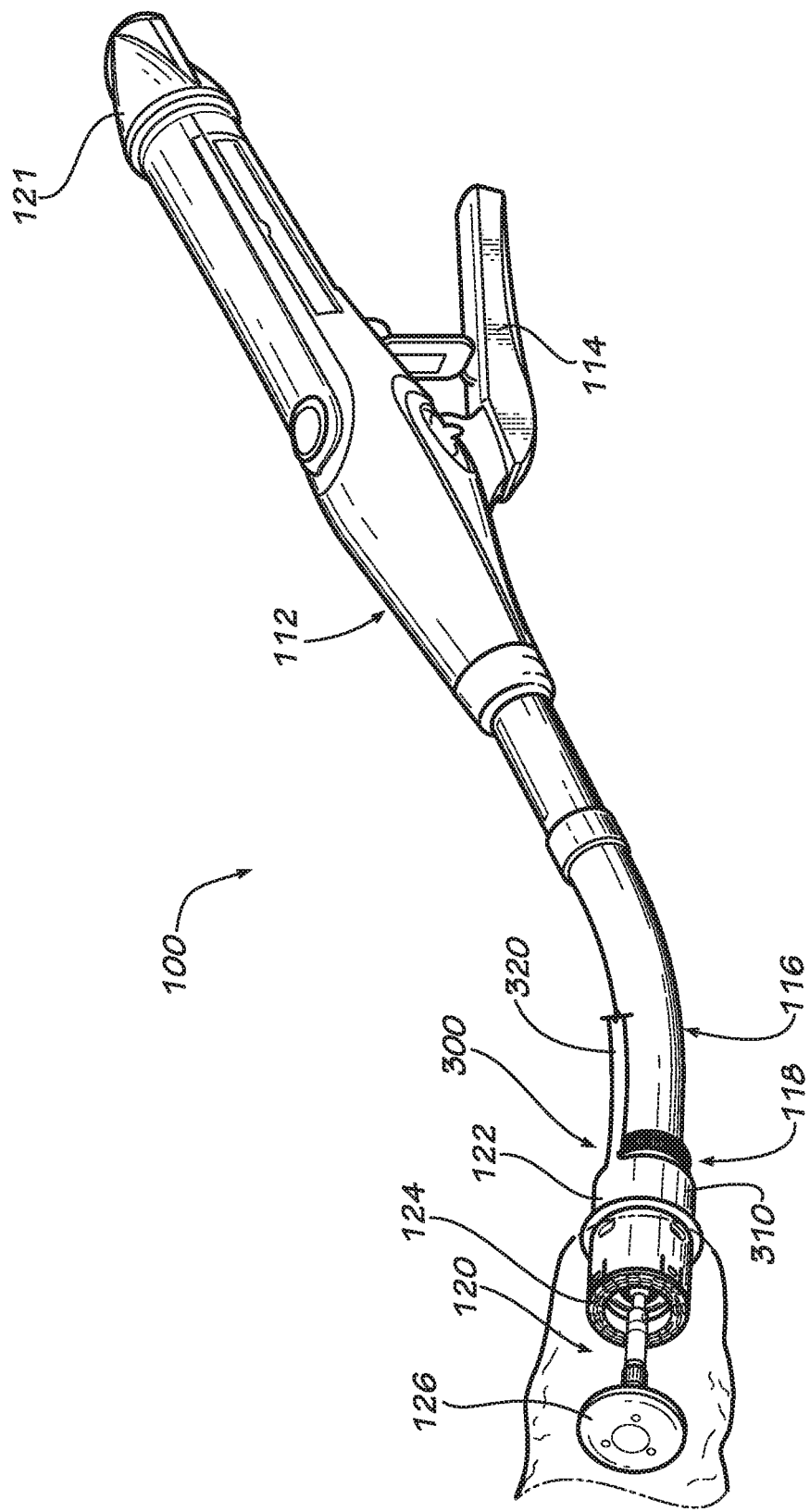
FIG. 2 is a perspective view of a manually operated circular stapling apparatus including the channel guide engaged therewith, and with a distal end of the circular stapling apparatus disposed within tissue, in accordance with embodiments of the present disclosure.

FIG. 2 illustrates a manually operated circular stapling apparatus 100 in accordance with embodiments of the present disclosure. Circular stapling apparatus 100 includes a handle assembly 112, an elongated member 116 extending distally therefrom, a tool assembly 118, which may be removably or fixedly coupled to the elongated member 116, and an end effector 120. The elongated body 116 extends distally from a distal end portion of the handle assembly 112 to a proximal end portion of the tool assembly 118. End effector 120 includes a shell assembly 122 that is configured to support a cartridge assembly 124 thereon, and an anvil assembly 126. Cartridge assembly 124 is configured to house a plurality of fasteners (not shown) and includes a corresponding plurality of pusher members that are substantially identical to pusher members 25 (FIG. 8) and which are operatively engagable with the fasteners (not shown). Anvil assembly 126 is supported to move in relation to cartridge assembly 124 between spaced and approximated positions and includes a plurality of pockets or depressions (not explicitly shown) that are configured to receive and deform corresponding fasteners when the fasteners are deployed from cartridge assembly 124. The handle assembly 112 includes a rotatable advancing member 121 for longitudinally moving anvil assembly 126 with respect to cartridge assembly 124 and a pivotable trigger member 114 for ejecting fasteners from cartridge assembly 124. Additionally, a channel guide 300 including a mounting portion 310 and an elongate passageway 320 is coupled to the shell assembly 122.

Further details of circular stapling apparatuses are disclosed in U.S. Patent Application Publication No. 2014/0252062 filed on Feb. 21, 2014, U.S. Patent Application Publication No. 2014/0197225, filed on Jan. 11, 2013, U.S. Pat. Nos. 8,806,973 and 9,010,609, the entire contents of each of which are hereby incorporated herein by reference.

Figure 3:
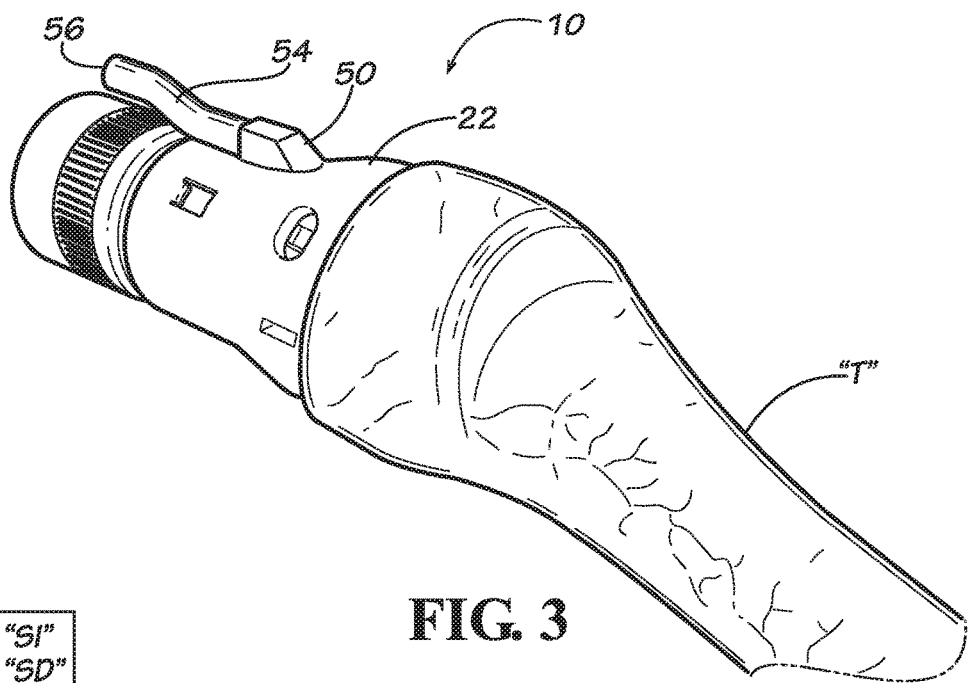
FIG. 3 is a perspective view of a shell assembly of a circular stapling apparatus including a port, shown partially inserted within a tissue lumen.
Figure 4:
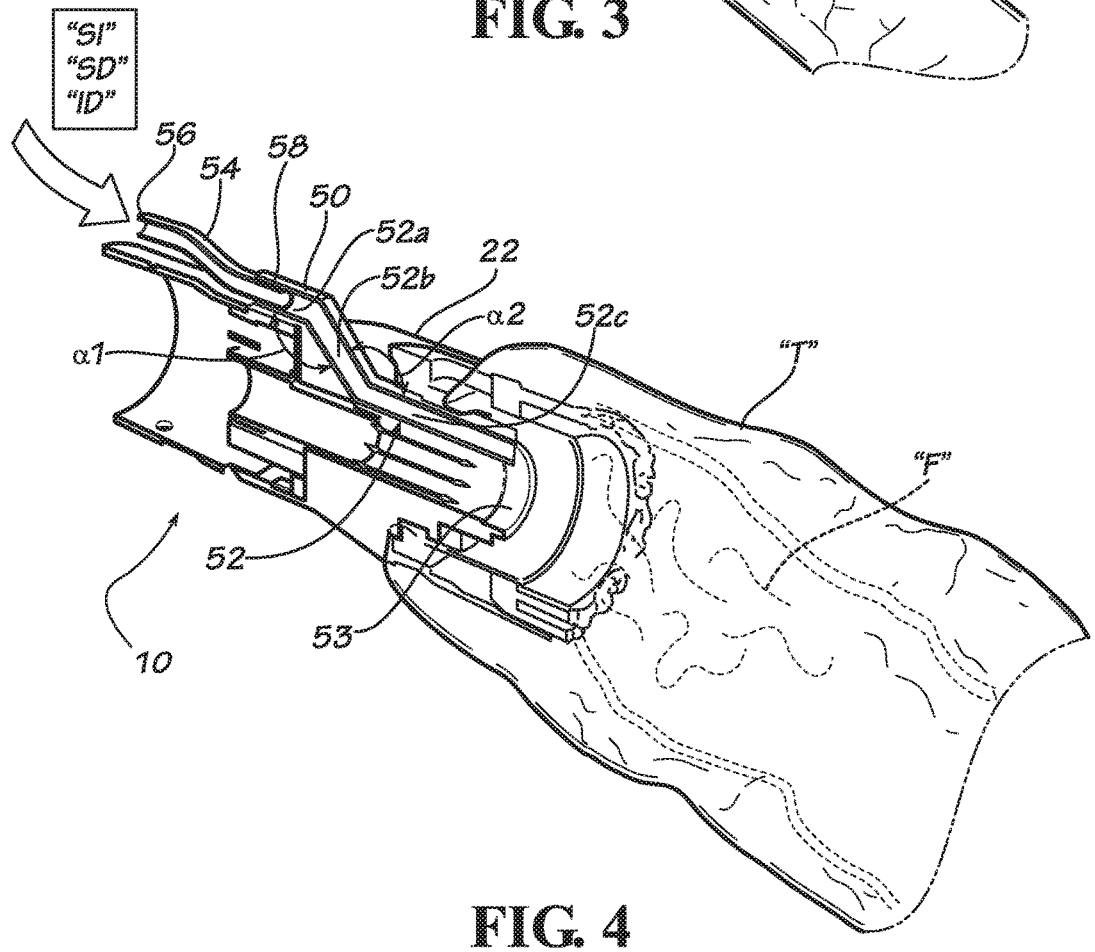
FIG. 4 is a partial, cut-away view of the shell assembly shown in FIG. 3 shown with fluid being introduced through the port and into the tissue lumen.
Figure 5:
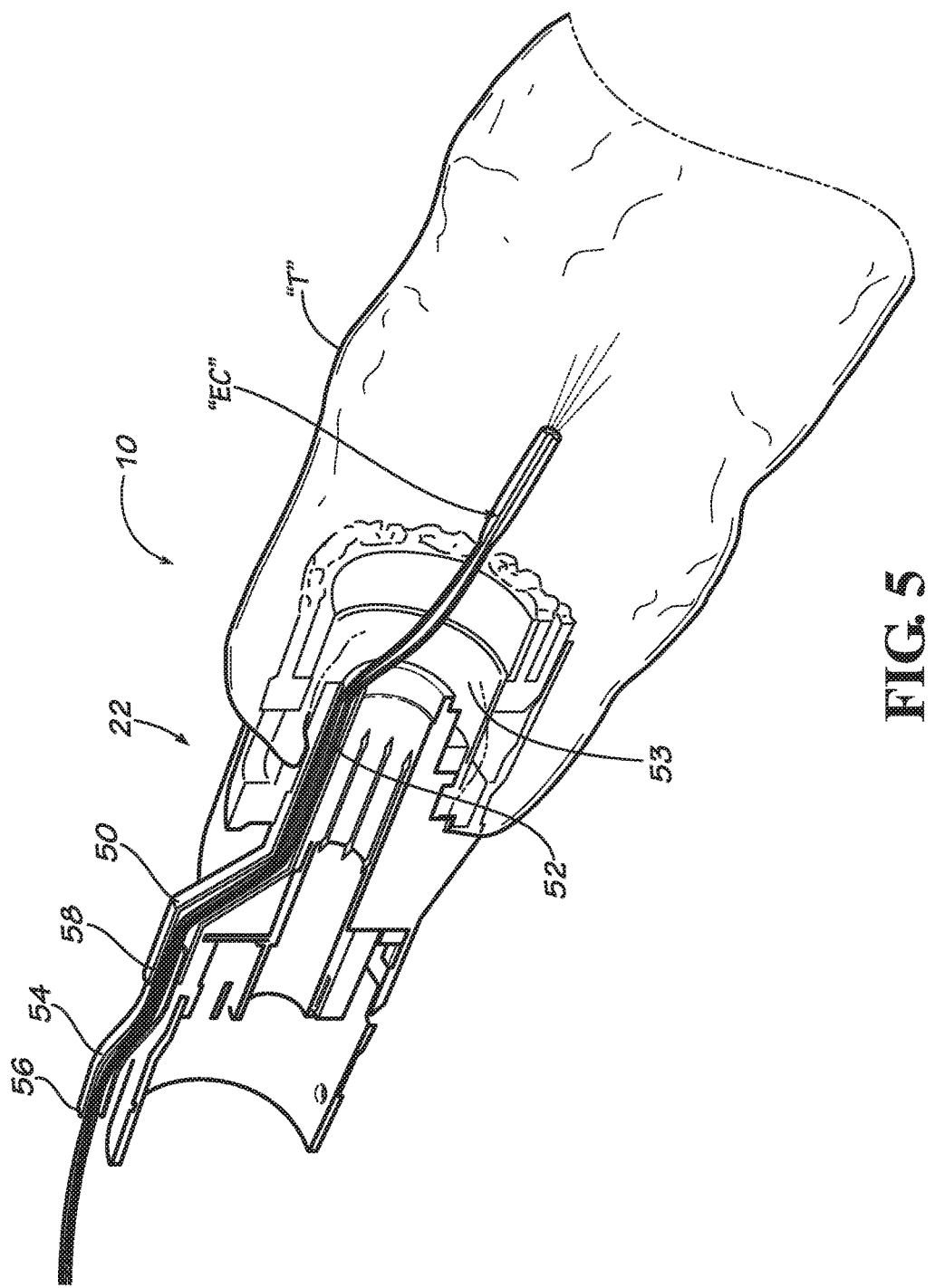
FIG. 5 is a partial, cut-away view of the shell assembly shown in FIG. 3 shown with an endoscopic camera extending through the port and within the tissue lumen.
Figure 6:
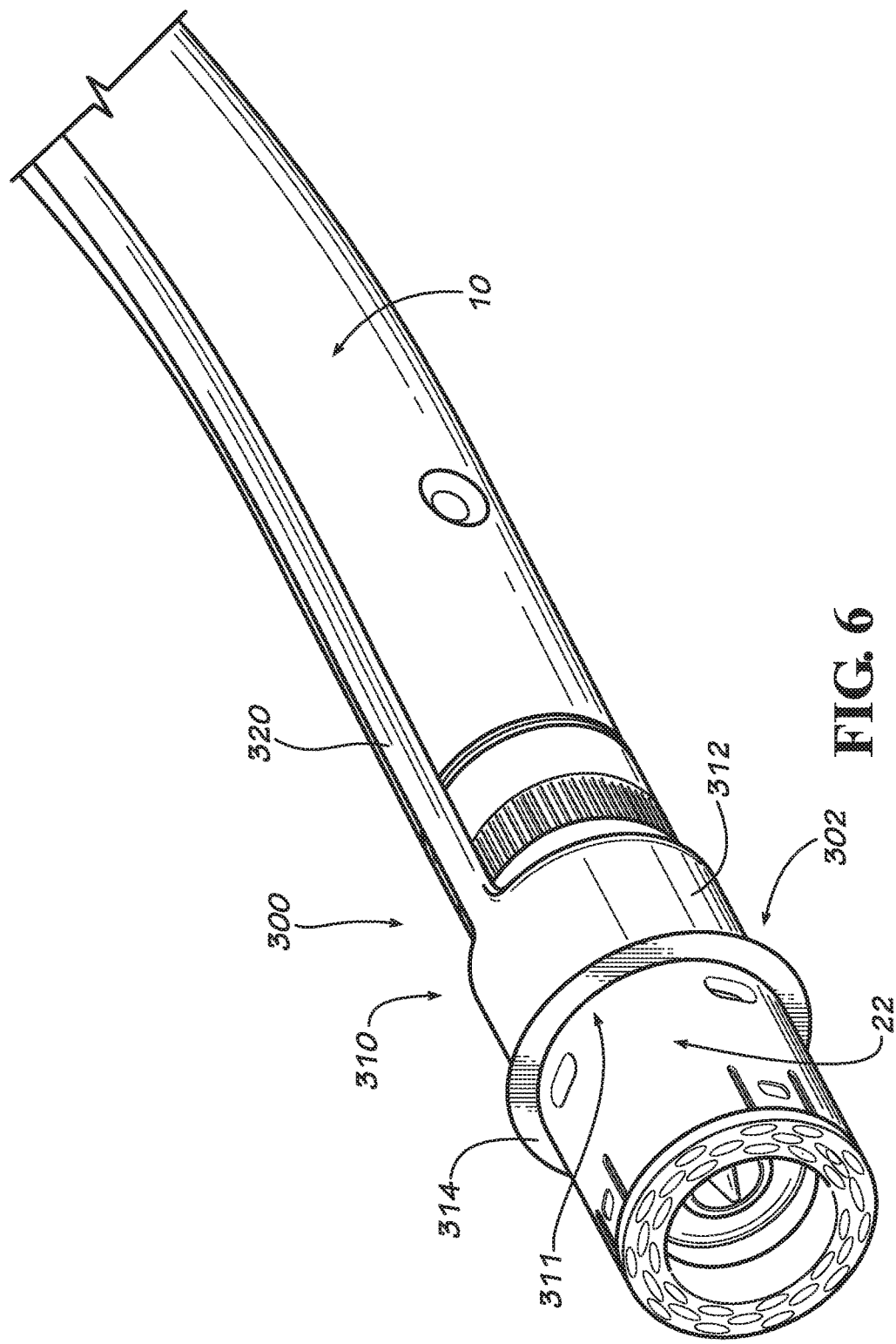
FIG. 6 is a perspective view of a portion of the channel guide coupled to the shell assembly of the circular stapling apparatus shown in FIG. 1, according to embodiments of the present disclosure.
Figure 7:
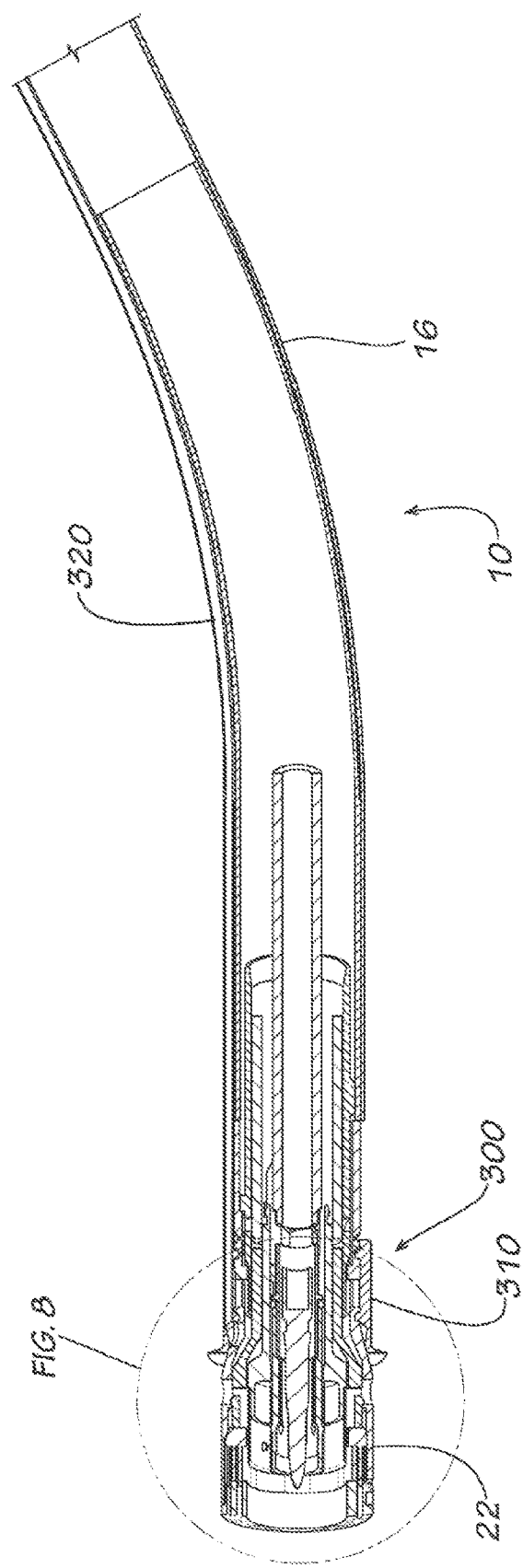
FIG. 7 is a cross-sectional view of the portion of the channel guide and the circular stapling apparatus shown in FIG. 6.

With particular reference to FIGS. 3-5, embodiments of circular stapling apparatus 10 are shown. Additionally, while circular stapling apparatus 100 is not explicitly shown in FIGS. 3-5, the features disclosed in FIGS. 3-5 are also applicable to the embodiments of circular stapling apparatus 100. Here, instead of channel guide 30, shell assembly 22 includes a port 50 disposed thereon. Port 50 is formed on an exterior wall of the shell assembly 22 and is configured to receive an elongated and/or flexible instrument (e.g., an endoscopic camera "EC," a tube associated with an irrigation device "ID" and/or a suction device "SD, etc.) therethrough, such that a portion of the elongated instrument can access the surgical site. Other surgical instruments that may be received in the port 50 for passage to the surgical site may include, but are not limited to, endoscopic graspers, endoscopic forceps, and endoscopic electrosurgical devices, which are shown schematically as "SI" in FIG. 4. The port 50 also provides an inlet for fluid "F" through the shell assembly 22 to a surgical site, and an outlet for fluid from the surgical site though the shell assembly 22, as will be described in detail below.

The port 50 is in fluid communication with a lumen 52 defined or secured within the shell assembly 22. The lumen 52 has a proximal end that is in fluid communication with port 50 and a distal, open end that may be positioned adjacent a distal end of a circular knife 53, for example, which is provided in the shell assembly 22 to sever stapled tissue sections. As shown in FIG. 4, the lumen 52 includes a first or proximal portion 52a, a second or intermediate portion 52b, and a third or distal portion 52c, which together define lumen 52 having a stepped or non-linear configuration. That is, the proximal portion 52a is disposed at an angle $\alpha 1$ with respect to the intermediate portion 52b, and the intermediate portion 52b is disposed at an angle $\alpha 2$ with respect to the distal portion 52c. It is envisioned that angle $\alpha 1$ may be between about 120° and about 150°; in embodiments angle $\alpha 1$ may be equal to about 135°. It is envisioned that angle $\alpha 2$ may be between about 120° and about 150°; in embodiments angle $\alpha 2$ may be equal to about 135°. It is further envisioned that angle $\alpha 1$ may be equal to or different from angle $\alpha 2$. Alternatively, other lumen configurations are envisioned.

A guide channel in the form of a hose 54 is couplable to the port 50 of the shell assembly 22. The hose 54 may provide a passageway to the port 50 for a surgical instrument being inserted through the port 50, e.g., an irrigation device "ID" or suction device "SD." In the embodiment illustrated in FIGS. 3-5, the hose 54 is formed from a material that is relatively flexible (e.g., plastic, rubber, etc.). Alternatively, the hose 54 may be formed from a material that is relatively rigid (e.g. plastic, metal, etc.).

In embodiments, the hose 54 extends longitudinally at least partially along the elongated member 16, 116 (FIGS. 1 and 2) and may be fixedly secured to a portion of the circular stapling apparatus 10 (e.g., the shell assembly 22, the elongated member 16, and/or the handle assembly 12) via one or more suitable securement methods (e.g., low tack adhesives, clips, bands, press- or friction-fit, etc.), not explicitly shown. It is further envisioned that hose 54 can be any reasonable length and may extend beyond the circular stapling apparatus 10.

A distal portion 58 (FIG. 4) of the hose 54 may be coupled to the port 50 via one or more suitable coupling methods, e.g., adhesive, welding, etc. In embodiments, the distal portion 58 of the hose may be removably coupled to the port 50 such that the port 50 may receive different types of hoses and/or different sizes of hoses. In this instance, the port 50 and the distal portion 58 of the hose 54 may couple to one another via a press- or friction-fit connection, a mechanical interface, or other suitable coupling methods. Alternatively, hose 54 may slidingly engage port 50 without any connection therebetween.

With particular reference to FIG. 4, the hose 54 includes a proximal end 56 that is configured to engage an irrigation device "ID," a suction device "SD," and/or another surgical instrument "SI," which are shown schematically in FIG. 4 as a single unit. Such irrigation/suction devices are known in the art and, therefore, are not described in further detail.

In embodiments, after an anastomosis has been created, the irrigation device "ID" can be coupled to the port 50 or the proximal end 56 of the hose 54 to circulate one or more suitable fluids "F" (e.g., saline, $CO_2$, etc.) through the hose 54 and/or port 50, and through the lumen 52 to the anastomosis site. As described above, introducing such fluids "F" into the colonic tract, for example, can be useful to check for leaks adjacent the anastomosis. The suction device "SD" may be coupled to the port 50 or the proximal end 56 of the hose 54 to remove fluid "F" from the anastomosis site, or to remove and/or suction other matter from the anastomosis site, e.g., tissue, etc.

In some embodiments, fluids "F" can be introduced to the anastomosis site during insertion of the stapling apparatus 10. By introducing fluids "F" into the anastomosis site during insertion of the stapling apparatus 10, the volume of the tissue lumen "T" can be increased to facilitate an injury-free insertion of the stapling apparatus 10 to the anastomosis site. Additionally or alternatively, introducing fluids "F" into the anastomosis site may lubricate the tissue lumen "T" to facilitate friction-free insertion of the stapling apparatus 10.

Additionally, other devices may be coupled to or extend through port 50. Such devices include endoscopic cameras "EC", guide wires, etc. Referring to FIG. 5, endoscopic camera "EC" is shown extending through hose 54 and port 50, and is within a tissue lumen "T." Endoscopic cameras are known in the art and, therefore, are not described herein in further detail. In embodiments, before and/or after an anastomosis has been created, a distal end of the endoscopic camera "EC" may be inserted through the hose 54 and/or port 50 of the shell assembly 22, and through the lumen 52 to the anastomosis site, for example. As described above, a user may use the endoscopic camera "EC" to inspect the anastomosis for bleeding, patency, and/or blood perfusion, for instance.

Additionally, it is envisioned that the stepped nature of lumen 52 helps maintain surgical instruments "SI" at a desired position within tissue. For example, when a flexible surgical instrument "SI" is inserted through the stepped lumen 52 such that a distal end of the surgical instrument "SI" is within tissue, the surgical instrument "SI" is less likely to move proximally with respect to the shell assembly 22 because of the non-linear path of the stepped lumen 52. That is, a surgical instrument "SI" will be physically hindered as it travels through a stepped lumen 52. By contrast, if the lumen 52 were linear, movement of fluid within the body tissue, contact between the surgical instrument "SI" and tissue, etc. may cause the surgical instrument "SI" to freely translate proximally or distally through such a linear lumen and thus not be optimally positioned.

Although only one port 50 is shown on the shell assembly 22 (FIG. 5), it is envisioned that the shell assembly 22 may include a plurality of ports 50 that are positioned on the exterior surface thereof. In these embodiments, each port 50 may be in fluid communication with the lumen 52 defined in the shell assembly 22. Alternatively, each port 50 may be in fluid communication with a corresponding lumen of a plurality of lumens 52 defined in the shell assembly 22. In such embodiments, for example, the suction device "SD" can be coupled to a first port, and an endoscopic camera "EC" can be coupled to a second port.

In embodiments, the port 50 may extend longitudinally at least partially along the tool assembly 18 and/or the elongated member 16 of the circular stapling apparatus 10. Additionally, the port 50 may be monolithically formed with the tool assembly 18 and/or the elongated member 16. As can be appreciated, in such embodiments, hose 54 may be omitted.

It is envisioned that the lumen 52 can extend from the shell assembly 22 to the handle portion 12 (e.g., to a proximal end of the handle portion 12). In such embodiments, the port 50 is positioned on the handle portion 12 and allows endoscopic camera "EC," irrigation device "ID," and/or suction device "SD" to be inserted from a location adjacent the handle portion 12, through at least a majority of the circular stapling apparatus 10, and into fluid communication with the anastomosis site, for example.

Referring to FIGS. 6-9 a channel guide 300 according to embodiments of the present disclosure is illustrated. In FIGS. 6-9, the channel guide 300 is shown coupled to the circular stapling apparatus 10. Channel guide 300 is configured to engage (either fixedly or removably) shell assembly 22 of circular stapling apparatus 10.

Channel guide 300 includes a mounting portion 310 and an elongate passageway 320 extending proximally therefrom. Mounting portion 310, which defines a longitudinal aperture 311, is sized and configured to mechanically engage shell assembly 22 of circular stapling apparatus 10.

More particularly, shell assembly 22 can be inserted (e.g., in a proximal-to-distal direction) at least partially through longitudinal aperture 311 of mounting portion 310. That is, mounting portion 310 can be positioned onto shell assembly 22 in a distal-to-proximal direction. In such embodiments, a distal portion 302 of channel guide 300 can flex radially outwardly to allow a portion of shell assembly 22 having a larger outer diameter "OD" than an inner diameter "ID" of channel guide 300 to be inserted into the mounting portion 310. Further, and with particular reference to FIG. 8, channel guide 300 includes inwardly depending lip(s) or rib 321 (e.g., annular lips 321) configured to be received within recess(es) 262 (e.g., annular recesses 262) of shell assembly 22. It is envisioned that the receipt of between lip(s) 321 within recess(es) 262 helps longitudinally align and sealingly secure the channel guide 300 to the shell assembly 22. It is further envisioned that alternatively or in addition to lip(s) 321 and recess(es) 262, channel guide 300 may be attached to shell assembly 22 with an adhesive.

It is also disclosed to mechanically engage channel guide 300 and circular stapling instrument 10 by first inserting elongated member 16 through longitudinal aperture 311 of mounting portion 310, then engaging shell assembly 22 with a distal end of elongated member 16, and then moving mounting portion 310 distally with respect to shell assembly 22. Here, too, lip(s) 321 is received within recess(es) 262 to help longitudinally align and sealingly secure the channel guide 300 to shell assembly 22.

Mounting portion 310 includes a body 312 defining an aperture 330 and a lumen 322 therein. Aperture 330 extends through a wall of body 312 and is disposed in fluid communication with lumen 322, which extends through body 312 and through elongate passageway 320 of channel guide 300. Additionally, aperture 330 of mounting portion 310 is configured to align with an opening 250 extending through an outer wall of shell assembly 22 that is in fluid communication with an interior space of shell assembly 22. Thus, the lumen 322 of elongate passageway 320 of channel guide 300 is in fluid communication with opening 250 of shell assembly 22, and with the interior space of shell assembly 22. In disclosed embodiments, as shown in FIGS. 1 and 2, elongate passageway 320 is a tube that extends externally of and parallel to elongate body 116. A proximal end of elongate passageway 320 may be disposed proximally of handle assembly 112, aligned with a portion of handle assembly 112, or disposed distally or handle assembly 112. As can be appreciated, devices (e.g., an endoscopic camera "EC") and/or fluid "F" can travel through a proximal end of elongate passageway 320, into the interior space of shell assembly 22, and to the surgical site.

It is envisioned that aperture 330 extends around a portion (e.g., majority or entirety) of a perimeter of mounting portion 310, thus facilitating radial alignment between aperture 330 and opening 250 of shell assembly 22. Additionally, the engagement between annular lip(s) 321 and annular recess(es) 262 may facilitate and/or enable the relative rotation of channel guide 300 with respect to shell assembly 22, e.g., to help align aperture 330 with opening 250 to provide a pathway to the surgical site.

In the illustrated embodiments, a distal end of mounting portion 310 includes a flange 314 extending along an outer periphery thereof. It is envisioned that flange 314 provides a surface for a user to grasp to facilitate coupling the channel guide 300 to the shell assembly 22, for example. While flange 314 is shown on a distal part of mounting portion 310, it is envisioned that flange 314 can be disposed on a different part of mounting portion 310 (e.g., on a proximal part thereof), and that mounting portion 310 can include more than one flange 314 thereon. For instance, it is envisioned that mounting portion 310 includes a first flange 314 on a proximal part thereof, and a second flange 314 on a distal part thereof.

It is further envisioned that channel guide 300 includes a seal member or grommet disposed in mechanical cooperation with aperture 330 and/or with a portion of lumen 322 to help seal or otherwise contain air or fluid pressurizations within tissue and/or to prevent spillage of such fluid.

Methods of using circular stapling apparatus 10, 100 and/or channel guide 300, as described above, are also disclosed herein. Additionally, the present disclosure includes methods of coupling channel guide 300 with circular stapling apparatus 10, 100, as disclosed herein.

For example, disclosed methods of performing a surgical procedure include selectively engaging channel guide 300 with circular stapling apparatus 10, aligning aperture 330 of channel guide 300 with opening 250 of shell assembly 22, performing a surgical procedure with circular stapling apparatus 10, and transporting at least one of a fluid "F" or a device (e.g., an endoscopic camera "EC") through aperture 330 of channel guide 300.

Additionally, embodiments of the disclosed methods include positioning channel guide 300 in engagement with circular stapling apparatus 10 such that elongate passageway 320 of channel guide 300 is disposed externally to and adjacent elongated member 16 of circular stapling apparatus 10, aligning an aperture 311 of mounting portion 310 of channel guide 300 with opening 250 of shell assembly 22 of circular stapling apparatus 10, performing a surgical procedure with circular stapling apparatus 10, and introducing at least one of a fluid "F" or surgical instrument "SI" through elongate passageway 320 of channel guide 300 and through aperture 311 of mounting portion 310 of channel guide 300.

Further aspects of the methods include positioning channel guide 300 in a distal-to-proximal direction to mechanically engage shell assembly 22 of circular stapling apparatus 10, and rotating mounting portion 310 of channel guide 300 with respect to shell assembly 22 while channel guide 300 is engaged with circular stapling apparatus 10. It is envisioned that rotation of mounting portion 310 with respect to the shell assembly 22 helps orient a surgical instrument "SI" in a desired location within tissue with respect to the shell assembly 22, for example.

It is envisioned that channel guide 300 is usable with various different types of surgical instruments, including those that include a replaceable cartridge assembly 24. It is further envisioned that channel guide 300 can be engaged and disengaged with circular stapling apparatus 10, or that circular stapling apparatus 10 is manufactured to include channel guide 300 already engaged therewith.

Figure 10:
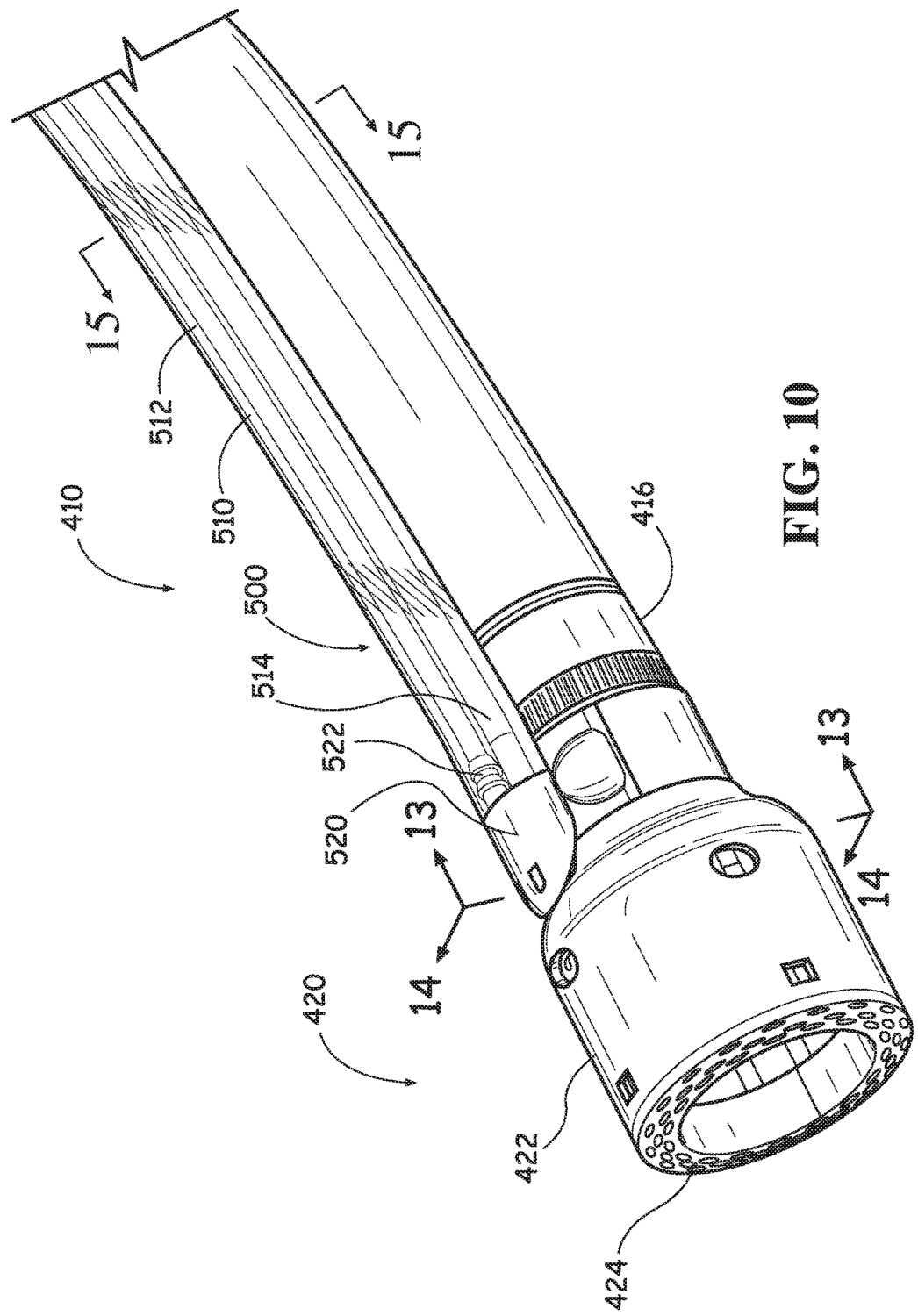
FIG. 10 is a perspective view of a circular stapling apparatus including an irrigation tube, in accordance with embodiments of the present disclosure.

Referring to FIGS. 10-14, embodiments of a circular stapling apparatus 410 are shown. The circular stapling apparatus 410 is similar to the circular stapling apparatus 10 detailed above with similar structures represented with reference numerals including a "4" preceding the previous reference numeral. Additionally, while circular stapling apparatuses 10 and 100 are not explicitly shown in FIGS. 10-14, the features disclosed in FIGS. 10-14 are also applicable to the embodiments of circular stapling apparatuses 10 and 100. With particular reference to FIG. 10, the circular stapling apparatus 410 includes an end effector 420 including a shell assembly 422 that is releasably coupled to an elongate member 416, and a guide channel or irrigation tube 500 that is coupled to the shell assembly 422.

Figure 11:
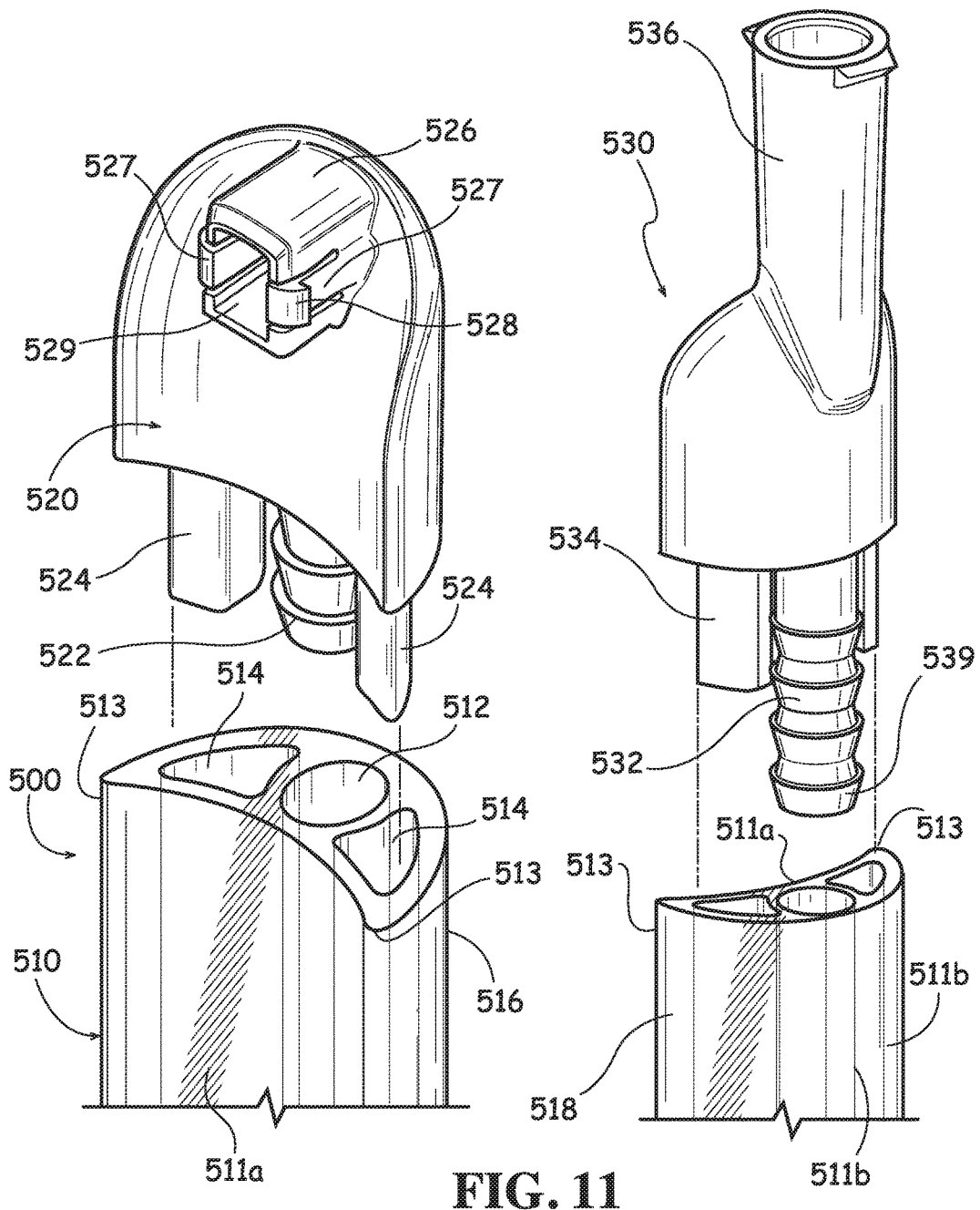
FIG. 11 is an exploded view with parts separated of the irrigation tube of FIG. 10.
Figure 15:
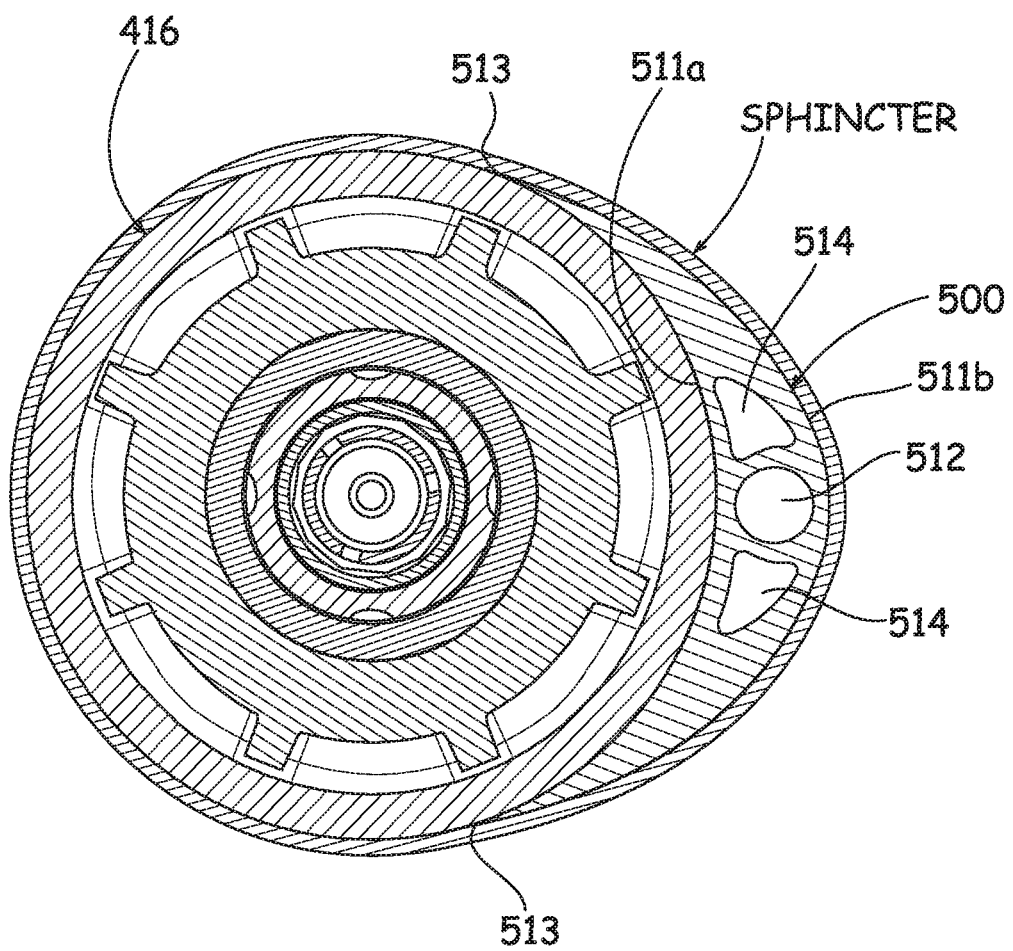
FIG. 15 is a cross-sectional view taken along section line 15-15 of FIG. 10.

Referring to FIG. 11, the irrigation tube 500 includes a flexible tube 510, a distal coupling 520, and a proximal coupling 530. The flexible tube 510 has a distal portion 516 and a proximal portion 518 and defines a central lumen 512 and two channels 514 positioned on either side of the central lumen 512 between distal and proximal portions 516, 518. The flexible tube 510 may be constructed from a clear plastic that is extruded to form the flexible tube 510. The flexible tube 510 has an inner surface 511$a$ and an outer surface 511$b$. The inner surface 511$a$ has a radius substantially equal to a radius of an outer surface of the elongate member 416 (FIG. 10) of circular stapling apparatus 410 such that the inner surface 511$a$ is in substantial contact with the elongate member 416 when the distal coupling 520 is secured to the shell assembly 422 as detailed below. With reference momentarily to FIG. 15, the surface profile of inner surface 511$a$ (e.g., the radius of curvature) is such that application of fluid/moisture (F) to inner surface 511$a$ of irrigation tube 500 helps to adhere irrigation tube to elongate member 416 of circular stapling apparatus 410 by way of a suctioning effect.

The outer surface 511b of the flexible tube 510 has a radius slightly less than the radius of the inner surface 511a such that the outer surface 511b meets the inner surface 511a at edges 513. The outer surface 511b is shaped such that the outer surface 511b forms a smooth transition with the outer surface of the elongate member 416 when the distal coupling 520 is secured to the shell assembly 422 as detailed below. With reference to FIG. 15, the smooth transition between the outer surface 511b of the flexible tube 510 and the outer surface of the elongate member 416 allows a sphincter (S) to form a seal about the elongate member 416 with the irrigation tube 500 attached. Specifically, the smooth transition eliminates gaps between the flexible tube 510 and the elongate member 416 which may prevent a sphincter from fully sealing about the elongate member 416 when the irrigation tube 500 is attached, for example, as is the case with other irrigation tubes having transverse cross-sectional profiles that are circular or of other shape.

The distal coupling 520 includes a central connector 522 that extends proximally into the central lumen 512 defined by the flexible tube 510. The central connector 522 may include ribs that engage walls defining the central lumen 512 to prevent the distal coupling 520 from separating from flexible tube 510. The distal coupling 520 also includes one or more proximally extending protrusions 524 (FIG. 11) that are each received within one of the passages 514 of the flexible tube 510 to secure the distal coupling 520 with the flexible tube 510. Each protrusion 524 may be shaped to conform to the shape of a respective passage 514. The distal coupling 520 also includes a nipple 526 that is substantially orthogonal to the central connector 522. The nipple 526 and the central connector 522 define a coupler lumen 529 that is in fluid communication with the central lumen 512 of the flexible tube 510 when the central connector 522 is received within the central lumen 512. The nipple 526 also includes tabs 527 on opposite sides of the nipple 526 and includes outer detents 528 that are configured to engage the shell assembly 422 to couple the distal coupling 520 to the shell assembly 422 as detailed below. The tabs 527 are resilient and biased outward.

The proximal coupling 530 includes a central connector 532 that extends distally into the central lumen 512 defined by the flexible tube 510. The central connector 532 may include ribs that engage walls defining the central lumen 512 to prevent the proximal coupling 530 from separating from flexible tube 510. The proximal coupling 530 also includes one or more distally extending protrusions 534 that are received within one of the passages 514 of the flexible tube 510 to secure the proximal coupling 530 with the flexible tube 510. Each protrusion 524 may be shaped to conform to the shape of a respective passage 514. The proximal coupling 530 includes a proximally extending connection 536 that is configured to couple to a fluid source. As shown, the proximally extending connection 536 is a male luer connector but it is contemplated that the proximally extending connection 536 may be a female luer connector or another known fluid coupling device. The proximally extending connection 536 and the central connector 532 define a coupler lumen 539 that is in fluid communication with the central lumen 512 when the central connector 532 is received within the central lumen 512.

It is contemplated that the protrusions 524 and 534 may define openings in fluid communication with the respective passages 514 and that the proximal coupling 530 and the distal coupling 520 may include additional connectors to fluidly connect the passages with a fluid source and to the circular stapling apparatus 410. In addition, the nipple 526 and/or the proximally extending connection 536 may be segmented such that a single connection may provide three distinct fluid channels between the distal and proximal couplings 520, 530. It is envisioned that each of the channels may provide a fluid to or withdraw a fluid from the circular stapling apparatus 410.

Figure 12:
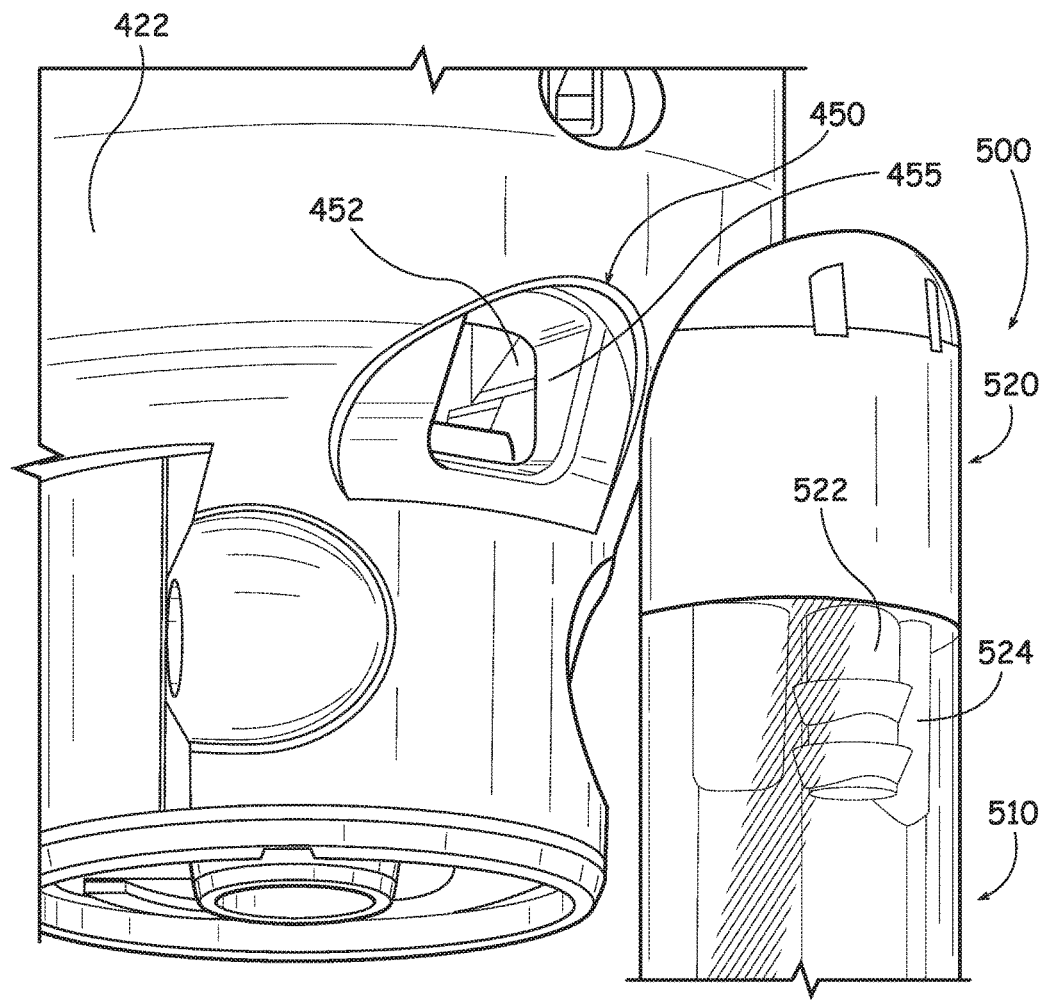
FIG. 12 in an enlarged view of the shell assembly of the circular stapling apparatus of FIG. 10 with the irrigation tube positioned adjacent a port of the shell assembly.
Figure 13:
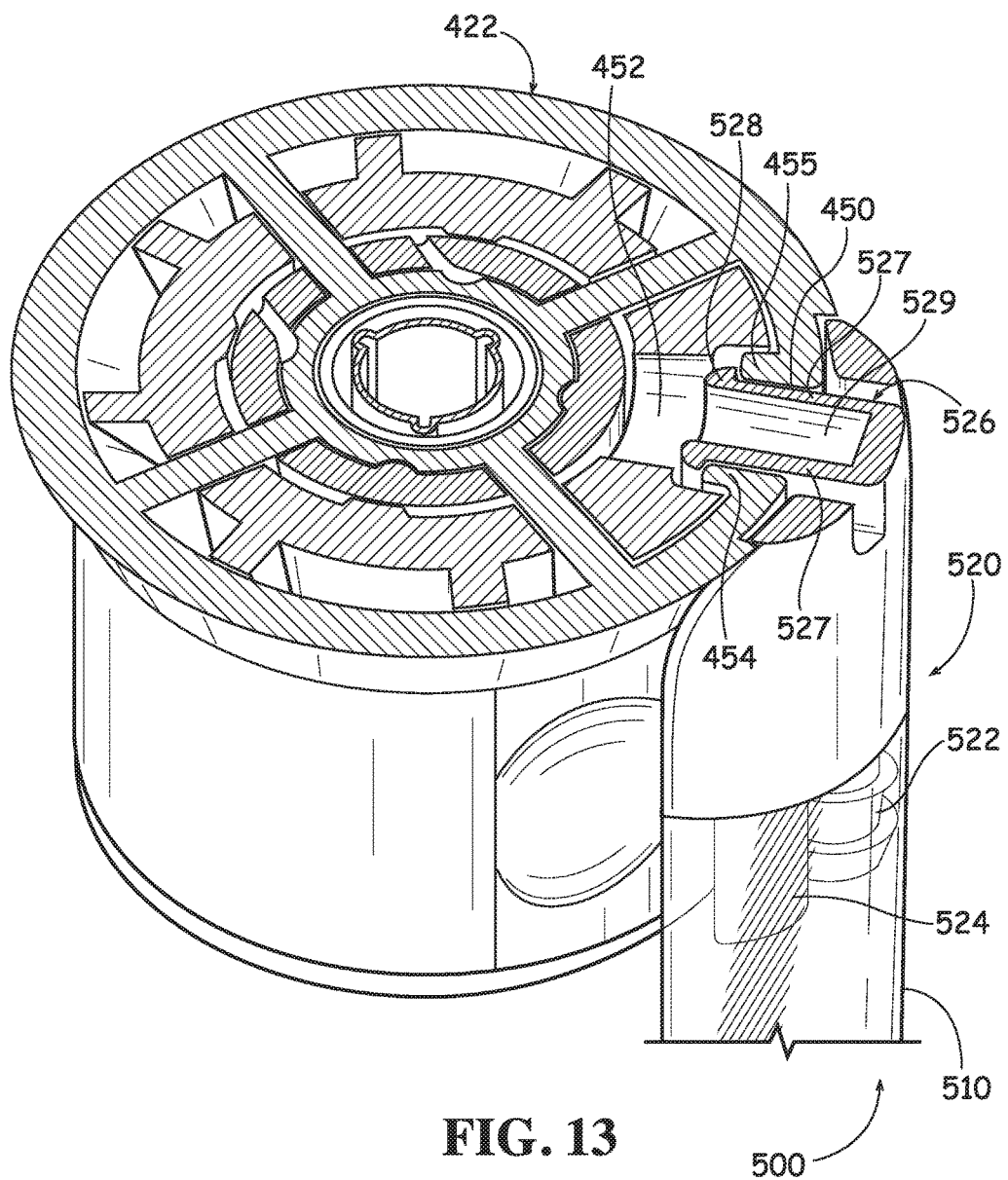
FIG. 13 is a cross-sectional view taken along the section line 13-13 of FIG. 10.
Figure 14:
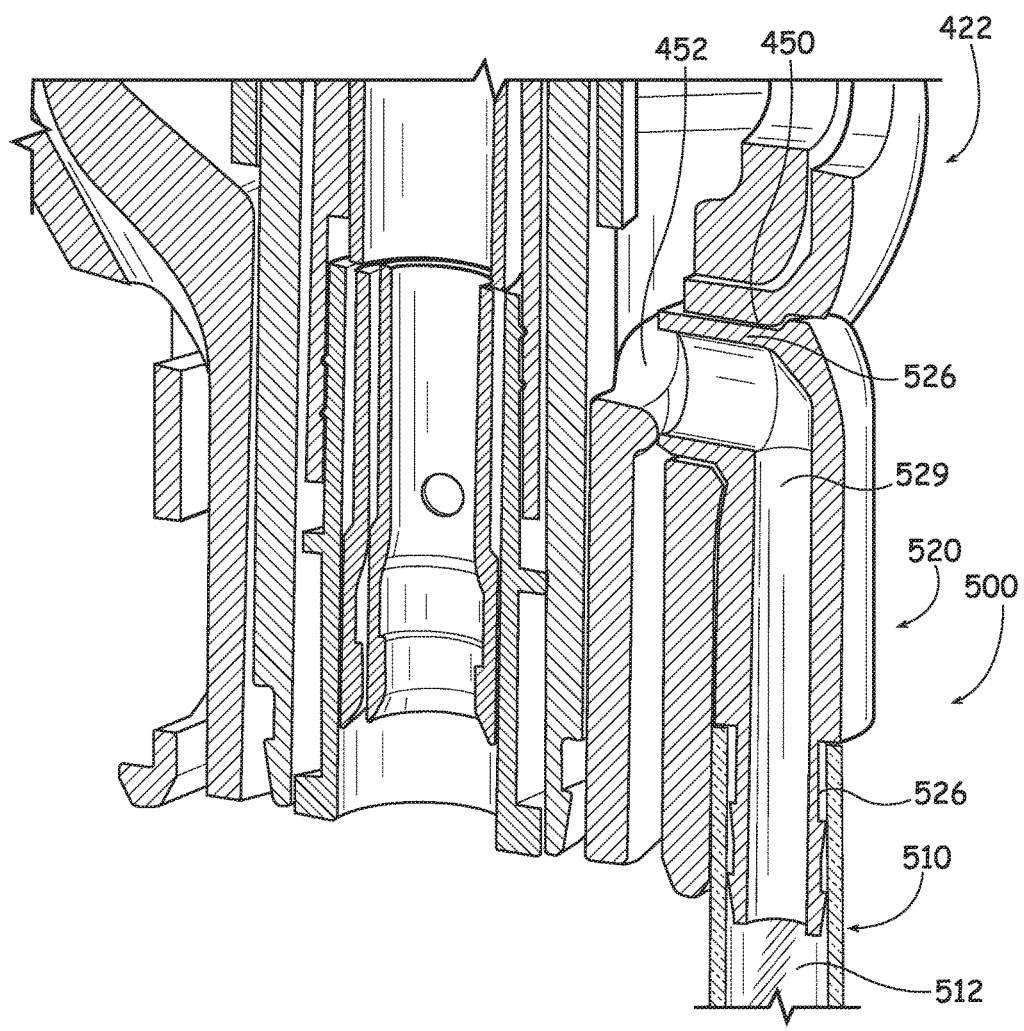
FIG. 14 is a cross-sectional view taken along the section line 14-14 of FIG. 10.

Referring now to FIGS. 12-14, the shell assembly 422 defines an opening or port 450 that is in fluid communication with a lumen 452 defined within the shell assembly 422. The lumen 452 passes through the shell assembly 422 such that the port 450 is in fluid communication with an anastomosis site through the lumen 452. The port 450 is defined by walls 455 that extend inward from an outer surface of the shell assembly 422.

With reference to FIG. 13, the nipple 526 of the distal coupling 520 of the irrigation tube 500 is coupled to the port 450 of the shell assembly 422. As the nipple 526 is inserted into the port 450, the detents 528 engage the walls 454 such that the tabs 527 are urged inwardly as the nipple 526 enters the port 450. When the detents 528 extend past the walls 455, the resilience of the tabs 527 snap the detents 528 outward to engage an inner surface of the walls 455 to couple the distal coupling 520 to the port 450. When the distal coupling 520 is coupled to the port 450, the nipple 526 seals the port 450 such that fluid may flow into the lumen 452 of the shell assembly 422 from the central lumen 512 of the irrigation tube 500 and/or from the lumen 452 of the shell assembly 422 into the central lumen 512 of the irrigation tube 500. As shown, when the distal coupling 520 is coupled to the shell assembly 422, the irrigation tube 500 is non-removably attached to the shell assembly 422. However, it is contemplated that the irrigation tube 500 may include a release mechanism (not shown) that allows the distal coupling 520 to releasably couple to the shell assembly 422.

With particular reference to FIGS. 3-5, a method of inserting the stapling apparatus 10 into a tissue lumen "T" in accordance with the present disclosure is disclosed. While detailed herein below with reference to apparatus 10, it will be appreciated that the method may also be used with stapling apparatuses 100 and 410. Initially, the stapling apparatus 10 is brought into close proximity with the tissue lumen "T" such that the shell assembly 22 can be inserted into an end of the tissue lumen "T" as shown in FIG. 3.

With the shell assembly 22 positioned within the end of the tissue lumen "T", an insufflation fluid "F" is introduced through the port 50 defined in the shell assembly 22. The insufflation fluid "F" can be a liquid, e.g., saline, that lubricates the tissue lumen "T" and increases the volume of the tissue lumen "T" to facilitate atraumatic insertion of the shell assembly 22 into the tissue lumen "T". When the tissue lumen "T" is insufflated to an appropriate degree, the stapling apparatus 10 can be advanced to the anastomosis site as detailed above.

After the stapling apparatus 10 is advanced to the anastomosis site, the stapling apparatus 10 is fired. After the stapling apparatus 10 is fired, the stapling apparatus 10 is removed from the patient. It has been shown that additional insufflation fluid "F" can be introduced through the port 50 as the stapling apparatus 10 is removed from the patient to assist in removing the stapling apparatus 10 from the patient. Specifically, the additional insufflation fluid "F" may expand the tissue lumen "T" and/or lubricate the tissue lumen "T" to assist in removing the stapling apparatus 10 from the tissue lumen "T".

The irrigation tube 500 may be provided as a part of a kit with a surgical stapling apparatus, e.g., surgical stapling apparatus 10, 100, 410.

From the foregoing and with reference to the various figure drawings, those skilled in the art will appreciate that certain modifications can also be made to the present surgical stapling apparatuses without departing from the scope of the same. While several embodiments of surgical stapling apparatuses have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. A method of inserting a circular stapling apparatus into a body lumen, the method comprising:
   inserting a distal portion of a shell assembly of the circular stapling apparatus into an entrance to a body lumen;
   introducing an insufflation fluid through an aperture defined in an outer surface of a proximal portion of the shell assembly such that the insufflation fluid flows into the body lumen; and
   inserting a remainder of the shell assembly and a portion of an elongated member of the circular stapling apparatus into the body lumen;
   wherein introducing the insufflation fluid through the aperture includes inserting a hose through a port communicating with the aperture such that the hose extends from within the shell assembly into the body lumen.

2. The method according to claim 1, wherein introducing the insufflation fluid through the aperture includes the insufflation fluid being a liquid which lubricates the body lumen.

3. The method according to claim 1, wherein introducing the insufflation fluid through the aperture includes increasing a volume of the body lumen.

4. The method according to claim 1, further comprising engaging a channel guide with the aperture of the shell assembly.

5. The method according to claim 4, wherein engaging the channel guide with the aperture of the shell assembly includes positioning a mounting portion of the channel guide about the shell assembly.

6. The method according to claim 4, wherein engaging the channel guide with the aperture of the shell assembly includes moving the mounting portion of the channel guide in a distal-to-proximal direction to mechanically engage the shell assembly.

7. A method of inserting a circular stapling apparatus into a body lumen, the method comprising:
   inserting a distal portion of a shell assembly of the circular stapling apparatus into an entrance to a body lumen;
   introducing an insufflation fluid through an aperture defined in an outer surface of the shell assembly such that the insufflation fluid flows into the body lumen
   inserting a remainder of the shell assembly and a portion of an elongated member of the circular stapling apparatus into the body lumen; and
   engaging a channel guide with the aperture of the shell assembly;
   wherein introducing the insufflation fluid through the aperture includes introducing the insufflation fluid through a passageway defined by the channel guide, the passageway in fluid communication with the aperture.

8. A method of inserting a circular stapling apparatus into a body lumen, the method comprising:
   inserting a distal portion of a shell assembly of the circular stapling apparatus into an entrance to a body lumen;
   introducing an insufflation fluid through an aperture defined in an outer surface of the shell assembly such that the insufflation fluid flows into the body lumen
   inserting a remainder of the shell assembly and a portion of an elongated member of the circular stapling apparatus into the body lumen; and
   engaging a channel guide with the aperture of the shell assembly;
   wherein engaging the channel guide with the aperture of the shell assembly includes inserting a nipple of the channel guide into the aperture of the shell assembly.

9. The method according to claim 8, wherein inserting the nipple of the channel guide into the aperture includes securing the nipple to the shell assembly with tabs extending from the nipple.

10. A method of inserting a circular stapling apparatus into a body lumen, the method comprising:
    inserting a distal portion of a shell assembly of the circular stapling apparatus into an entrance to a body lumen;
    introducing an insufflation fluid through an aperture defined in an outer surface of the shell assembly such that the insufflation fluid flows into the body lumen
    inserting a remainder of the shell assembly and a portion of an elongated member of the circular stapling apparatus into the body lumen; and
    engaging a channel guide with the aperture of the shell assembly;
    wherein engaging the channel guide with the aperture of the shell assembly occurs after inserting the distal portion of the shell assembly of the circular stapling apparatus into a body lumen.

11. A method of inserting a circular stapling apparatus into a body lumen, the method comprising:
    inserting a distal portion of a shell assembly of the circular stapling apparatus into an entrance to a body lumen;
    introducing an insufflation fluid through an aperture defined in an outer surface of the shell assembly such that the insufflation fluid flows into the body lumen;
    inserting a remainder of the shell assembly and a portion of an elongated member of the circular stapling apparatus into the body lumen;
    engaging a channel guide with the aperture of the shell assembly; and
    rotating the mounting portion of the channel guide with respect to the shell assembly while the channel guide is engaged with the circular stapling apparatus;
    wherein engaging the channel guide with the aperture of the shell assembly occurs after inserting the distal portion of the shell assembly of the circular stapling apparatus into a body lumen.

12. A method of inserting a circular stapling apparatus into a body lumen, the method comprising:
    inserting a distal portion of a shell assembly of the circular stapling apparatus into an entrance to a body lumen;
    introducing an insufflation fluid through an aperture defined in an outer surface of the shell assembly such that the insufflation fluid flows into the body lumen
    inserting a remainder of the shell assembly and a portion of an elongated member of the circular stapling apparatus into the body lumen;
    engaging a channel guide with the aperture of the shell assembly; and advancing a camera distally through the channel guide, through the aperture, and to a surgical site wherein engaging the channel guide with the aperture of the shell assembly occurs after inserting the distal portion of the shell assembly of the circular stapling apparatus into a body lumen.

13. A method of inserting a circular stapling apparatus into a body lumen, the method comprising:

inserting a distal portion of a shell assembly of the circular stapling apparatus into an entrance to a body lumen;

introducing an insufflation fluid through an aperture defined in an outer surface of the shell assembly such that the insufflation fluid flows into the body lumen inserting a remainder of the shell assembly and a portion of an elongated member of the circular stapling apparatus into the body lumen; and engaging a channel guide with the aperture of the shell assembly; and advancing a guide wire through the channel guide, through the aperture, and to a surgical site;

wherein engaging the channel guide with the aperture of the shell assembly occurs after inserting the distal portion of the shell assembly of the circular stapling apparatus into a body lumen.

14. A method of removing a circular stapling apparatus from a body lumen, the method comprising:

withdrawing a distal portion of a shell assembly of a circular stapling apparatus from a body lumen; and introducing an insufflation fluid through an aperture defined in an outer surface of a proximal portion of the shell assembly such that the insufflation fluid flows into the body lumen while withdrawing the distal portion of the shell assembly;

wherein introducing the insufflation fluid through the aperture includes supplying the insufflation fluid through a hose in communication with a port communicating with the aperture such that the hose extends from within the shell assembly into the body lumen.

15. The method according to claim 14, wherein introducing the insufflation fluid through the aperture includes the insufflation fluid being a liquid which lubricates the body lumen.

16. The method according to claim 14, wherein introducing the insufflation fluid through the aperture includes increasing a volume of the body lumen.

* * * * *